US010335210B2

(12) United States Patent
Ricker et al.

(10) Patent No.: US 10,335,210 B2
(45) Date of Patent: Jul. 2, 2019

(54) ANATOMIC PLATES FOR MEDIAL PROXIMAL TIBIA

(71) Applicant: Biomet Manufacturing, LLC, Warsaw, IN (US)

(72) Inventors: Lauren Ricker, Columbia City, IN (US); Daniel S Horwitz, Danville, PA (US); Roy Sanders, Tampa, FL (US); Dan Dziadosz, Tampa, FL (US); Peter Giannoudis, Leeds (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 142 days.

(21) Appl. No.: 15/405,730

(22) Filed: Jan. 13, 2017

(65) Prior Publication Data

US 2017/0209194 A1 Jul. 27, 2017

Related U.S. Application Data

(60) Provisional application No. 62/281,372, filed on Jan. 21, 2016.

(51) Int. Cl.
*A61B 17/80* (2006.01)
*A61B 17/17* (2006.01)

(52) U.S. Cl.
CPC ...... *A61B 17/8014* (2013.01); *A61B 17/8057* (2013.01); *A61B 17/8061* (2013.01); *A61B 17/1764* (2013.01)

(58) Field of Classification Search
CPC ... A61B 17/80; A61B 17/8014; A61B 17/808; A61B 17/8061

USPC .................................................. 606/283–285
See application file for complete search history.

(56) References Cited

U.S. PATENT DOCUMENTS

| | | | |
|---|---|---|---|
| 7,771,433 B2 | 8/2010 | Orbay et al. | |
| 8,172,886 B2 | 5/2012 | Castaneda et al. | |
| 8,262,707 B2 | 9/2012 | Huebner et al. | |
| 8,317,842 B2 | 11/2012 | Graham et al. | |
| 8,740,905 B2 | 6/2014 | Price et al. | |
| 2006/0173458 A1* | 8/2006 | Forstein | A61B 17/1728 606/86 B |
| 2011/0218576 A1* | 9/2011 | Galm | A61B 17/8061 606/289 |
| 2012/0165878 A1 | 6/2012 | Hwa et al. | |
| 2013/0245696 A1* | 9/2013 | Raven, III | A61B 17/8061 606/280 |

(Continued)

FOREIGN PATENT DOCUMENTS

| | | |
|---|---|---|
| EP | 2476388 A1 | 7/2012 |
| WO | WO-2017127295 A1 | 7/2017 |

OTHER PUBLICATIONS

"International Application Serial No. PCT/US2017/013361, International Search Report dated May 9, 2017", 3 pgs.

(Continued)

*Primary Examiner* — Matthew J Lawson
(74) *Attorney, Agent, or Firm* — Schwegman Lundberg & Woessner, P.A.

(57) ABSTRACT

In one example, a bone plate comprises a proximal head extending from a first head end to a second head end, and a distal shaft connected to the proximal head and extending from a first shaft end to a second shaft end, wherein the proximal head is shaped to conform to a proximal medial portion of a tibia.

20 Claims, 9 Drawing Sheets

(56) References Cited

U.S. PATENT DOCUMENTS

2015/0327899 A1* 11/2015 Early ............... A61B 17/80
606/280

OTHER PUBLICATIONS

"International Application Serial No. PCT/US2017/013361, Written Opinion dated May 9, 2017", 5 pgs.

"3.5 mm LCP Medial Proximal Tibia Plates. Part of the synthes locking compression plate (LCP) system", Synthes, Technique, [Online]. Retrieved from the Internet: <URL: http://www.synthes.com/sites/NA/NAContent/Docs/Product%20Support%20Materials/Technique%20Guides/Test_Document_1J0101A.pdf>, (2006), 24 pgs.

"3.5 mm LCP Posteromedial Proximal Tibia Plates. Part of the synthes locking compression plate (LCP) system.", Synthes, Technique Guide, [Online]. Retrieved from the Internet: <URL: http://sites.synthes.com/mediabin/US%20DATA/Product%20Support%20Materials/Technique%20Guides/SUTG3.5LCPPosteromedialProxTibJ8804B.pdf>, (2009), 26 pgs.

"4.5 mm LCP Medial Proximal Tibia Plates. Part of the Synthes LCP Periarticular Plating System.", Synthes, Technique Guide, (2006), 32 pgs.

"Distal Tibia Plating System", Biomet ALPS, Surgical Technique, (2014), 44 pgs.

"LCP Medial Proximal Tibial Plate 4.5/5.0. Part of the Synthes LCP periarticular plating system.", Synthes, Technique Guide, (2007), 32 pgs.

"Numelock II Polyaxial Locking System", Stryker, Osteosynthesis, Operative Technique, and Trauma Applications, (2009), 40 pgs.

"OptiLock® Periarticular Plating System for Proximal Tibial Fractures", EBI: EBR Trauma, Pre-Launch Surgical Technique, (2006), 28 pgs.

"Periarticular Proximal Tibial Locking Plate", Zimmer® / Trauma, Surgical Technique, (2008), 20 pgs.

"Periarticular Proximal Tibial Locking Plate", Zimmer® / Trauma, Surgical Technique, (2008), 40 pgs.

"Proximal Tibia Plating System", Biomet APLS, Surgical Technique, (2012), 28 pgs.

"Proximal Tibia Variable-Angle Locking Plates", smith&nephew, PERI-LOC VLP Variable-Angle Locked Plating System, (Nov. 2007), 4 pgs.

* cited by examiner

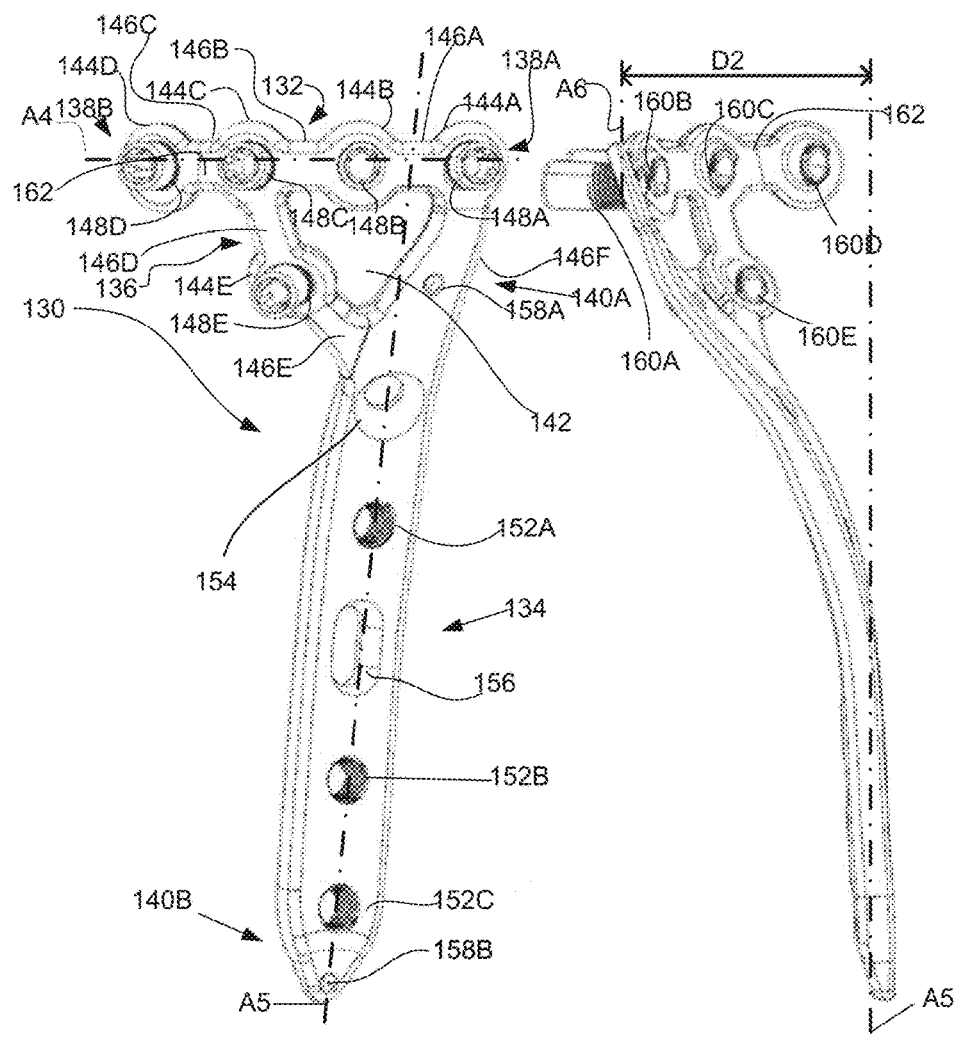
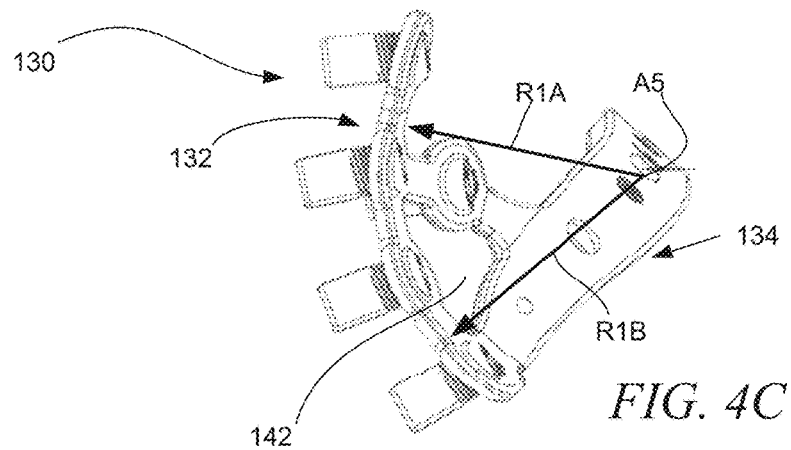
FIG. 4A    FIG. 4B
FIG. 4C

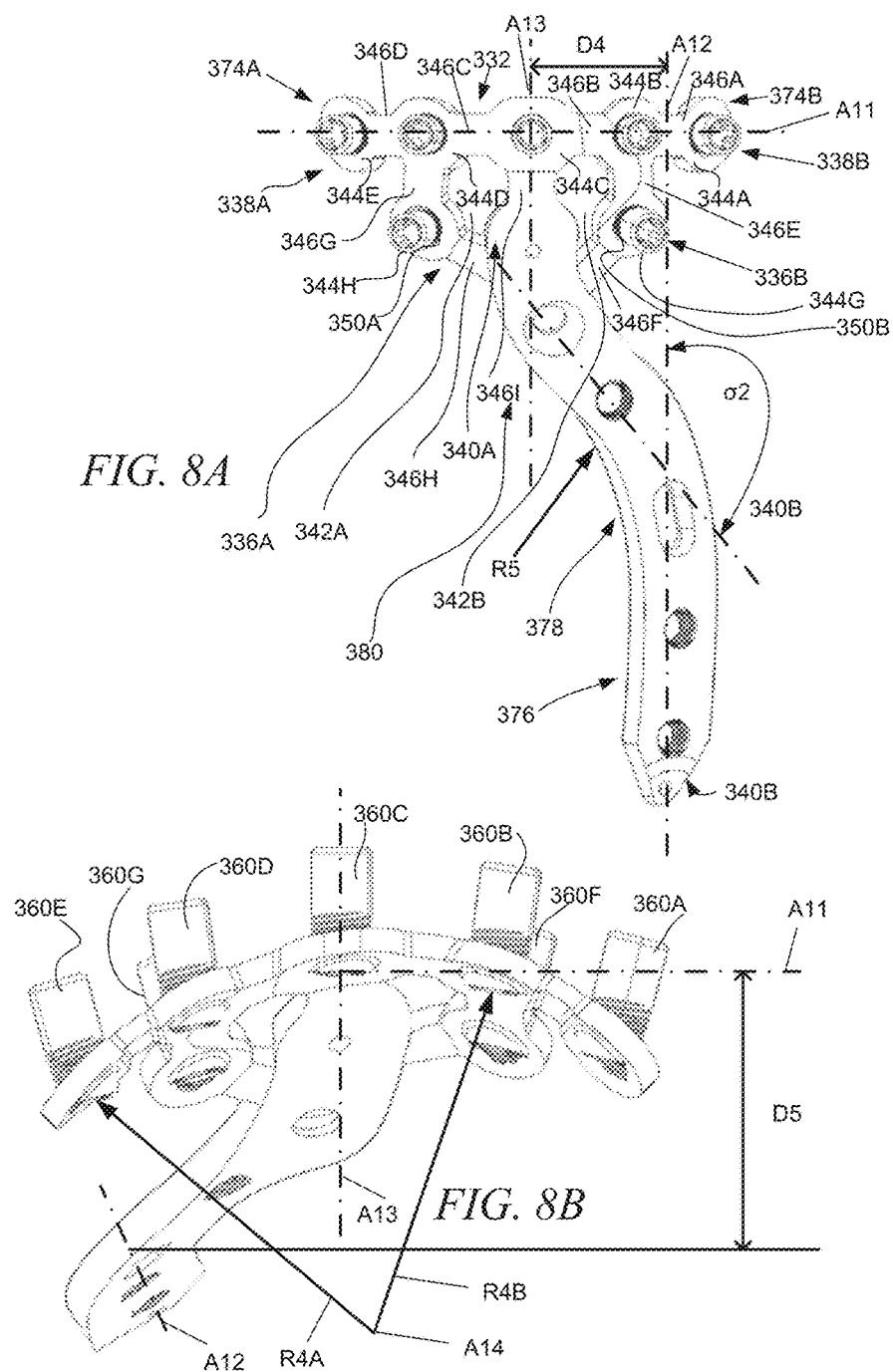

ANATOMIC PLATES FOR MEDIAL PROXIMAL TIBIA

CLAIM OF PRIORITY

This application claims the benefit of U.S. Provisional Patent Application Ser. No. 62/281,372, filed on Jan. 21, 2016, the benefit of priority of which is claimed hereby, and which is incorporated by reference herein in its entirety.

FIELD

Subject matter of the present application relates to orthopedic systems and specifically to surgical devices for the internal fixation of fractured bones, such as bone plates.

BACKGROUND

Bone plates can be used to treat fractured bones. Typically, a bone plate is secured to a bone to stabilize parts of a fractured bone while the bone mends. Periarticular bone plates are used to treat bone fractures adjacent a joint and typically include an elongate shaft portion which is secured to the diaphysis of a bone, and a flared head portion which is attached to the metaphysis of the bone with, e.g., a plurality of screws.

Currently available bone plates for the proximal tibia have a head portion extending from a shaft portion and are specifically configured to mount to a lateral side of the tibia. In some designs, the head portion can be offset from the shaft portion in the frontal plane so as to accommodate the anatomy, such as the Gerdy's tubercle region of the proximal tibia.

Example lateral proximal tibial bone plates are discussed in U.S. Pat. No. 8,262,707 to Huebner et al. and U.S. Pat. No. 8,740,905 to Price et al.

Overview

Anatomic plates for a medial proximal tibia are described that can facilitate repairing of damaged medial condyle portions on the tibia. The plates can have head portions and shaft portions. The head portions can be positioned on the medial condyle in anterior-medial, posterior-medial and direct medial positions. The shaft portions can be configured to be straight, curved or twisted to reach different portions of the diaphysis of the tibia. Such combinations of head and shaft portions can allow for direct support and reduction of damaged portions of the medial proximal tibia that might not be adequately reached with lateral proximal tibia plates.

To further illustrate the components and methods disclosed herein, a non-limiting list of examples is provided here:

In Example 1, a bone plate comprises: a proximal head extending from a first head end to a second head end, and a distal shaft connected to the proximal head and extending from a first shaft end to a second shaft end, wherein the proximal head is shaped to conform to a proximal medial portion of a tibia.

Example 2 can include, or can optionally be combined with the subject matter of Example 1, to optionally include a proximal head that is elongated along a first axis and a distal shaft that is elongated along a second axis approximately perpendicular to the first axis.

Example 3 can include, or can optionally be combined with the subject matter of Examples 1 and 2, to optionally include a strut connecting the proximal head with the distal shaft to leave an open interior region.

Example 4 can include, or can optionally be combined with the subject matter of Example 3, to optionally include a strut that comprises at least one hole portion flanked by at least one thinned region.

Example 5 can include, or can optionally be combined with the subject matter of Examples 3 and 4, to optionally include a proximal head that includes at least three locking holes, the strut includes a single locking hole, and a distal shaft portion that includes a plurality of locking holes, a multi-directional hole, a compression slot and a wire hole.

Example 6 can include, or can optionally be combined with the subject matter of Examples 1-4 to optionally include a proximal head that is shaped to conform to a medial condyle of the tibia.

Example 7 can include, or can optionally be combined with the subject matter of Examples 1-6, to optionally include a proximal head that is shaped to conform to an anterior medial portion of the medial condyle.

Example 8 can include, or can optionally be combined with the subject matter of Example 7, to optionally include a strut connecting the second end of the proximal head and a mid-section of the distal shaft, wherein the first head end is connected to the first shaft end, and the proximal head extends perpendicularly medially from the distal shaft.

Example 9 can include, or can optionally be combined with the subject matter of Example 8, to optionally include a proximal head that includes three locking holes, a strut that includes a single locking hole, and a distal shaft portion that includes a plurality of locking holes, a multi-directional hole and a compression slot.

Example 10 can include, or can optionally be combined with the subject matter of Examples 8 and 9, to optionally include a proximal head that is offset from the distal shaft portion in an anterior direction.

Example 11 can include, or can optionally be combined with the subject matter of Examples 1-6, to optionally include a proximal head is shaped to conform to a posterior medial portion of the medial condyle.

Example 12 can include, or can optionally be combined with the subject matter of Example 11, to optionally include a strut connecting a mid-section of the proximal head and a mid-section of the distal shaft, wherein the first head end is connected to the first shaft end, and the proximal head extends perpendicularly medially from the distal shaft.

Example 13 can include, or can optionally be combined with the subject matter of Example 12, to optionally include a proximal head that includes four locking holes, a strut that includes a single locking hole, and a distal shaft that includes a plurality of locking holes, a multi-directional hole and a compression slot.

Example 14 can include, or can optionally be combined with the subject matter of Examples 12 and 13, to optionally include a proximal head that is offset from the distal shaft in a posterior direction.

Example 15 can include, or can optionally be combined with the subject matter of Examples 12-14, to optionally include a proximal-section of the distal shaft that is offset from a distal-section of the distal shaft in a posterior direction.

Example 16 can include, or can optionally be combined with the subject matter of Examples 12-15, to optionally include a mid-section of the distal shaft that is curved such that the distal-section and the second shaft end of the distal shaft are positionable on an anterior medial side of a tibia.

Example 17 can include, or can optionally be combined with the subject matter of Examples 1-6, to optionally include a proximal head that is shaped to conform to a direct medial portion of the medial condyle.

Example 18 can include, or can optionally be combined with the subject matter of Example 17, to optionally include a first strut connecting a lateral mid-section of the proximal head portion to a mid-section of the distal shaft, and a second strut connecting a medial mid-section of the proximal head portion to the mid-section of the distal shaft, wherein a mid-point of the proximal head portion is connected to the first shaft end, and the proximal head extends perpendicularly medially and laterally from the distal shaft.

Example 19 can include, or can optionally be combined with the subject matter of Example 18, to optionally include a proximal head that includes five locking holes, each strut includes a single locking hole, and a distal shaft that includes a plurality of locking holes, a multi-directional hole and a compression slot.

Example 20 can include, or can optionally be combined with the subject matter of Examples 18 and 19, to optionally include a proximal head that is offset from the distal shaft in a medial direction, and a mid-section of the distal shaft portion that is curved such that the second shaft end of the distal shaft is positionable on an anterior medial side of a tibia.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 4A is a front view of a posterior medial straight bone plate, in accordance with at least one example of the present disclosure.

FIG. 4B is a side view of the posterior medial straight bone plate of FIG. 4A, in accordance with at least one example of the present disclosure.

FIG. 4C is a top view of the posterior medial straight bone plate of FIGS. 4A and 4B, in accordance with at least one example of the present disclosure.

FIG. 8A is a front view of a direct medial bone plate, in accordance with at least one example of the present disclosure.

FIG. 8B is a top view of the direct medial bone plate of FIG. 8A, in accordance with at least one example of the present disclosure.

DETAILED DESCRIPTION

Example medial proximal tibia bone plates are described. Head portions of the bone plates are contoured to mate closely with a metaphysis of a tibia, particularly the medial condylar portion. Shaft portions of the bone plates extend from the head portions to support the head portion along a diaphysis of the tibia. The head portion can include thinned regions that allow the head portion to be shaped intraoperatively. The head portion can also include one or more fixation holes to receive drill guides, fasteners and the like. The shaft portion can also include one or more fixation holes, including round, oblong, multi-directional, and locking holes, compression slots and wire holes.

Figure 1:
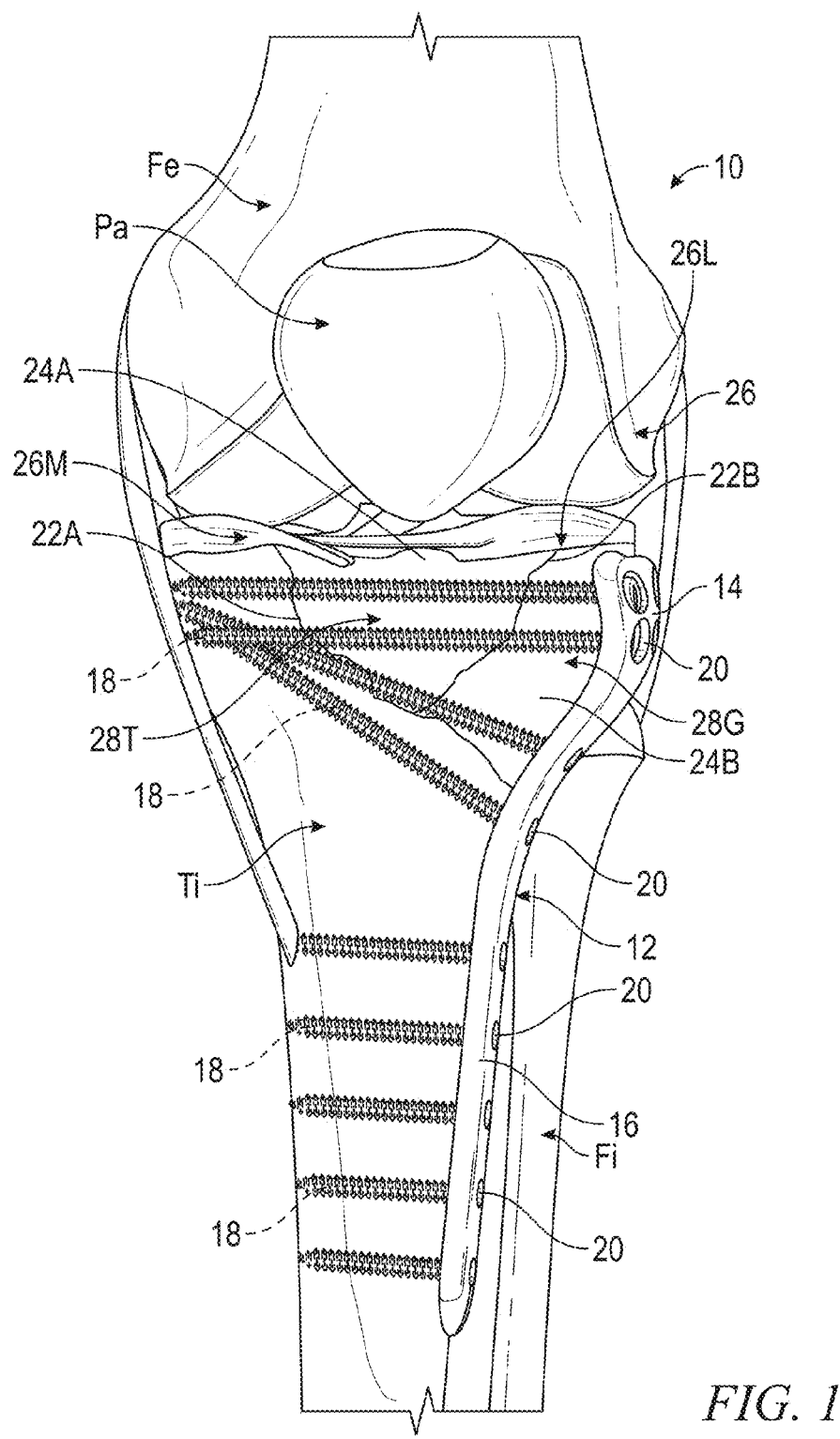
FIG. 1 is a schematic anterior view of a left knee joint showing a conventional lateral proximal tibia bone plate mounted to a lateral side of a tibia.

FIG. 1 is a schematic anterior view of left knee joint 10 showing conventional proximal tibia bone plate 12 mounted to a lateral side of tibia Ti. Knee joint 10 also includes femur Fe, patella Pa and fibula Fi. Proximal tibia bone plate 12 includes head portion 14 that connects to the metaphysis of tibia Ti, and shaft portion 16 that connects to the diaphysis of tibia Ti. Fasteners 18 are inserted through bores 20 within bone plate 12 to affix bone plate 12 to tibia Ti.

Tibia Ti includes fractures 22A and 22B such that bone fragments 24A and 24B of tibia Ti are produced, such as after tibia Ti has been subjected to a trauma. Conventional bone plates, as shown, require a surgeon to insert a plurality of fasteners 18 to reach all of the bone fragments. This sometimes requires the use of long fasteners to reach inaccessible fragments, such as fragment 24A, which is not directly reachable by proximal lateral bone plate 12. Furthermore, it is sometimes difficult to access various portions of tibia Ti due to the presence of muscle and operating room equipment. For example, the posterior side of tibia Ti is difficult to access due to the location of the calf muscle and the operating room table. Thus, it can be difficult to stabilize each of the portions of the proximal portion of tibia Ti, such as lateral condyle 26L, medial condyle 26M, Gurdy's Tubercle 28G and tibial tubercle 28T.

Figures 2A, 2B:
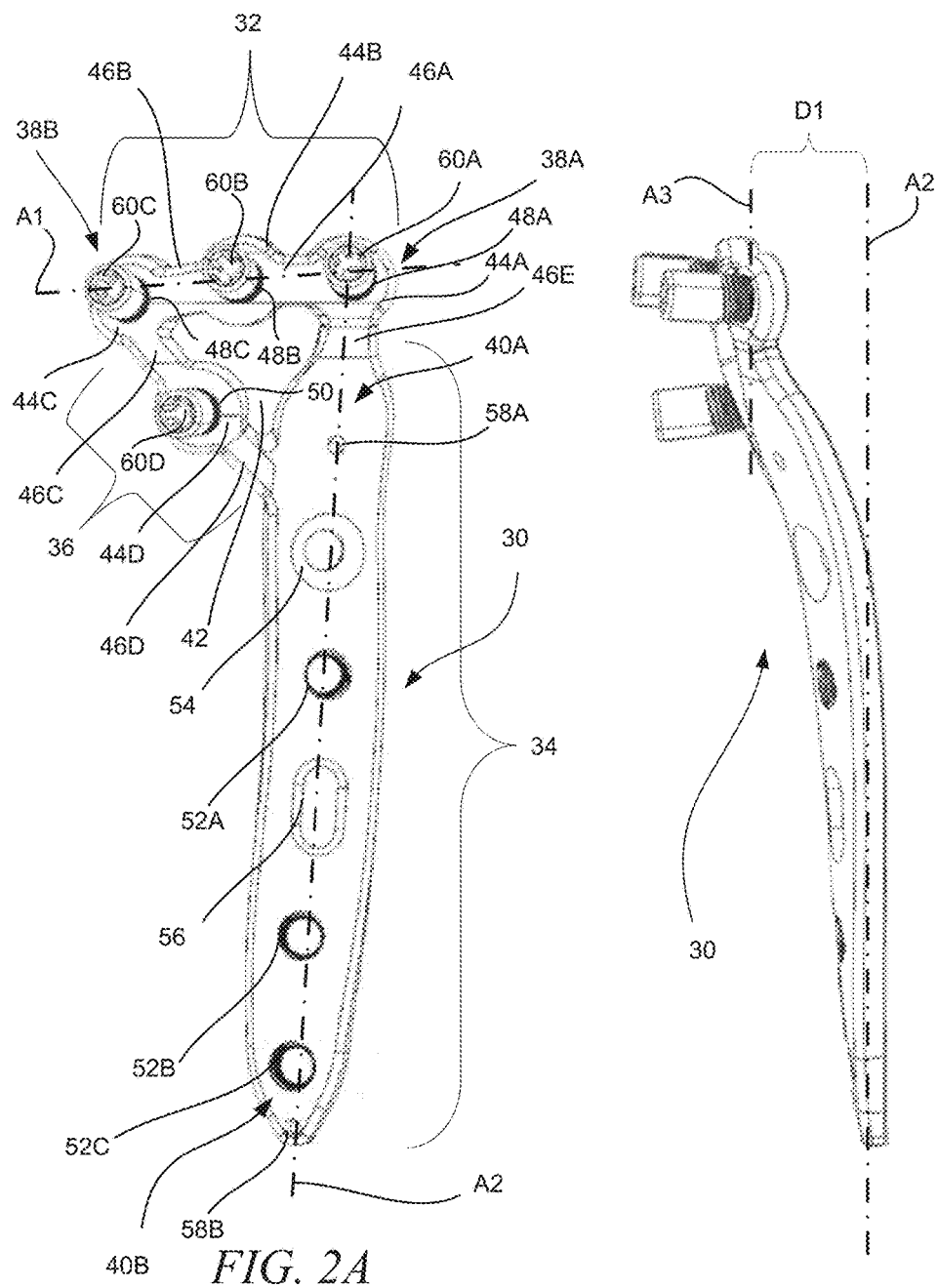
FIG. 2A is a front view of an anterior medial standard-sized bone plate, in accordance with at least one example of the present disclosure.
FIG. 2B is a side view of the anterior medial standard-sized bone plate of FIG. 2A, in accordance with at least one example of the present disclosure.

FIG. 2A is a front view of anterior medial standard-sized bone plate 30, which can include proximal head 32, distal shaft 34 and strut 36. FIG. 2B is a side view of anterior medial standard-sized bone plate 30 of FIG. 2A. FIGS. 2A and 2B are discussed concurrently. FIGS. 2A and 2B show bone plate 30 as being a left-hand specific bone plate. However, bone plate 30 can be configured as a right-hand specific bone plate, such as by producing a bone plate that is a mirror image of bone plate 30.

Proximal head 32 can be shaped to conform to a proximal medial portion of tibia Ti. In particular, proximal head 32 can be configured to conform to the anterior portion of medial condyle 26M of tibia Ti. Proximal head 32 can extend from first head end 38A to second head end 38B. In one example, proximal head 32 can be 2 mm thick.

Distal shaft 34 can extend from first shaft end 40A to second shaft end 40B. Distal shaft 34 can be configured to mate with an anterior medial face of the diaphysis of tibia Ti. In one example, distal shaft 34 can be 3 mm thick.

Proximal head 32 can be elongated along first axis A1 and distal shaft 34 can be elongated along second axis A2, which can be perpendicular, or near perpendicular, to first axis A1. In one example, proximal head 32 is approximately 30 mm long along first axis A1. In another example, a wide variant may be provided in which proximal head 32 is approximately 40 mm long along first axis A1. In such a wide variant, the lengths of thinned regions 44A, 44B, 44C and 44D may be increased to accommodate the wider size, thereby also increasing the footprint of interior region 42. It has been found that those two head sizes can provide sufficient support to the vast majority of tibia sizes. In one example, distal shaft 34 has a length along second axis A2 that is in the range of approximately 90 mm to approximately 360 mm in order to accommodate different sized tibias. It has been found that those shaft sizes can provide sufficient support to the vast majority of tibia sizes. In one example, distal shaft 34 is approximately 11.75 mm wide relative to second axis A2, and proximal head 32 is approximately 9 mm wide at hole portions 44 and approximately 2.5 mm wide at thinned regions 46, relative to first axis A1. Strut 36 can connect proximal head 32 with distal shaft 34 to leave open interior region 42.

As seen in FIG. 2B, proximal head 32 can be offset from distal shaft 34 via distance D1, as is represented by the offset between third axis A3 of proximal head 32 and second axis A2 of distal shaft 34. In one example, distance D1 can be approximately 10 mm. Such an offset has been found to be sufficient to wrap around the coronal curvature (i.e., curvature in a coronal plane) of the vast majority of medial condyles.

Proximal head 32 and strut 36 can each comprise at least one hole portion 44 flanked by at least one of thinned regions 46. In the disclosed embodiment, proximal head 32 can have three hole portions 44A, 44B and 44C, and strut 36 can have one hole portion 44D. Thinned region 46A can connect hole portion 44A and hole portion 44B. Thinned region 46B can connect hole portion hole portion 44B and hole portion 44C. Thinned region 46C can connect hole portion 44C and hole portion 44D. Thinned region 46D can connect hole portion 44D and distal shaft 34. In particular, thinned region 46D can connect to a mid-section of distal shaft 34. Thinned region 46E can connect hole portion 44A and distal shaft 34. In particular, thinned region 46E can connect to first shaft end 40A.

First head end 38A can connect to first shaft end 40A. First head end 38A can extend generally perpendicularly from distal shaft 34 to the medial side of distal shaft 34. Strut 36 can connect second head end 38B and a mid-section of distal shaft 34 between first shaft end 40A and second shaft end 40B to form interior region 42.

Bone plate 30 can include a plurality of holes to which various fasteners, pins and wires can be connected. Proximal head 32 can include three locking holes 48A, 48B and 48C. Strut 36 can include locking hole 50. Such a combination of locking holes has been found to be sufficient to reach the majority of the territory of medial condyle 26M with fixation screws.

Distal shaft 34 can include locking holes 52A, 52B and 52C, multi-directional hole 54, compression slot 56 and wire holes 58A and 58B. Drill guides 60A, 60B, 60C and 60D are shown connected to locking holes 48A, 48B and 48C, respectively. Drill guides 60A-60D may comprise drill guides as described in U.S. Pat. No. 8,172,886 to Castaneda et al., which is hereby incorporated by this reference in its entirety for all purposes. In one example, each of locking holes 52A-52C, multi-directional hole 54 and compression slot 56 can be spaced apart by 13 mm. It has been found that such combination of hole types and spacing allows bone plate 30 to be both easily mounted to tibia Ti and to provide sufficient support and reduction to proximal portions of tibia Ti anchored by distal shaft 34.

Locking holes 48A-48C, 50 and 52A-52C can include a threaded bore that allows a threaded shaft of a fastener, such as fasteners 18 of FIG. 1, to pass freely through. The threading of the bore is configured to engage mating threading on the head of the fastener in order to lock the fastener in place with a particular orientation relative to distal shaft 34. In one example, locking holes 48A-48C, 50 and 52A-52C can be configured to receive fixed angle bone fasteners described in U.S. Pat. No. 8,317,842 to Graham et al., which is hereby incorporated by this reference in its entirety for all purposes. In one example, locking holes 48A-48C, 50 and 52A-52C can have a cone shaped and can be configured to accept A.L.P.S. 4.0/3.5 mm screws, which are commercially available from Biomet, Inc. The threading of the bore can also be configured to receive a threading on drill guides 60A-60D.

Multi-directional hole 54 includes a countersink that allows the head of a fastener to recede into hole 54 while being angled relative to distal shaft 34 in a variety of orientations. Thus, multi-directional hole 54 does not lock a fastener into a particular orientation. As such, a surgeon can insert a fastener into hole 54 in a desired orientation to provide support to a specific region of a damaged tibia.

Compression slot 56 comprises an oblong bore, such as an oval or stretched circle, that is configured to receive a fastener and not lock the fastener into a particular orientation in addition to allowing the position of bone plate 30 to be adjusted while being held in place against tibia Ti. Compression slot 56 is also used to provide compression to aid in bone healing.

Wire holes 58A and 58B comprise through-bores that allow pins to be inserted into tibia Ti after the position of bone plate 30 is determined in order to allow other fasteners to be installed through locking holes 48A-48C, 50 and 52A-52C.

Figure 3:
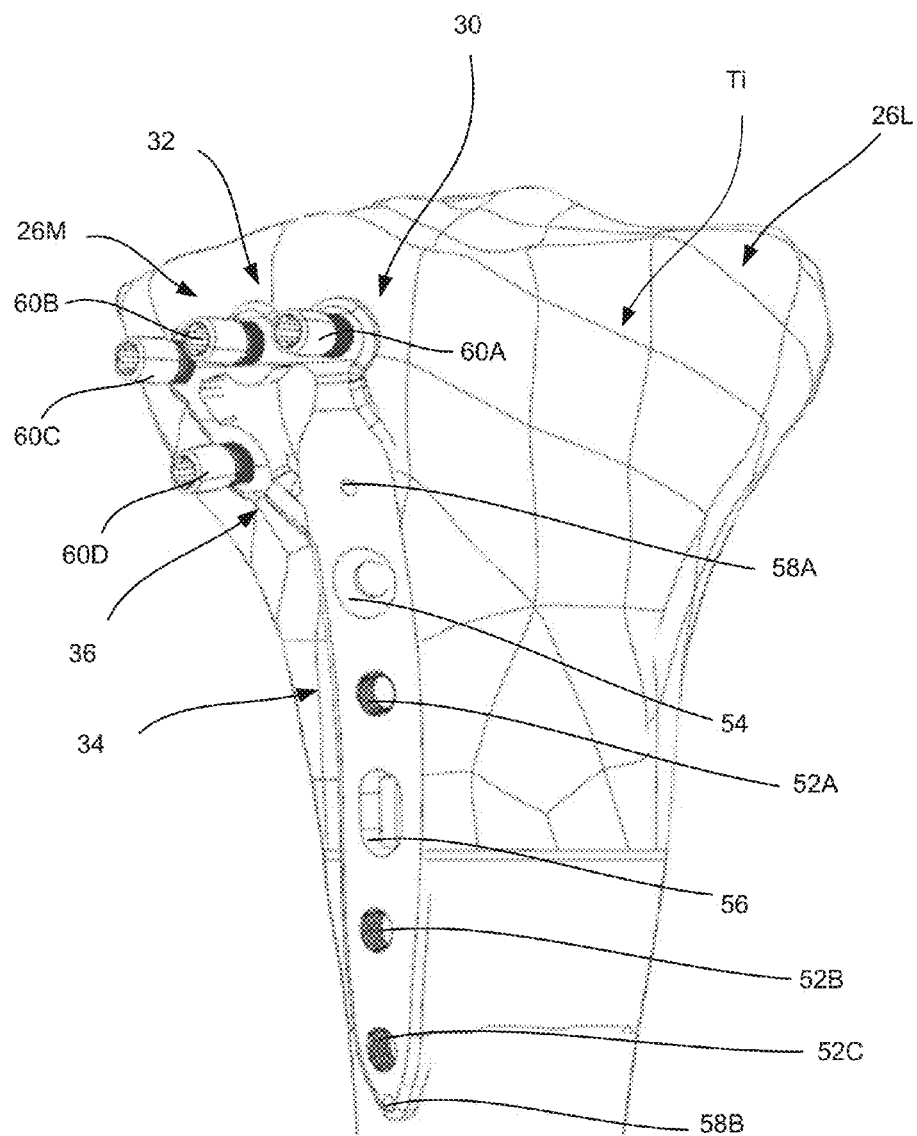
FIG. 3 is an anterior view of a proximal end of a tibia to which the bone plate of FIGS. 2A and 2B is mounted, in accordance with at least one example of the present disclosure.

FIG. 3 is an anterior view of a proximal end of tibia T1 to which bone plate 30 of FIGS. 2A and 2B is mounted. Proximal head 32 can extend across the anterior side of medial condyle 26M of tibia Ti. Distal shaft 34 can extend across the anterior side of the diaphysis of tibia Ti. As discussed below, thinned regions 46A-46E can be bent to conform to the various surfaces and contours of medial condyle 26M.

In order to install bone plate 30 on a proximal portion of tibia Ti, a surgeon can first locate the general location on the anterior medial portion of tibia Ti to which bone plate 30 is to be fit. Once in a rough position, in one option, a hole can be drilled in the location of compression slot 56. A fastener can be inserted through compression slot 56 and threaded into the drilled hole. In another option, wire holes 58A and 58B are first used to secure bone plate 30 to tibia Ti.

Next, hole portions 44A-44D can be adjusted by bending thinned regions 46A-46E. For example, thinned regions 46A-46E can be bent to conform bone plate 30 to the contours of the anterior medial portion of tibia Ti. Drill guides 60A-60C can be used to facilitate bending of bone plate 30, as is described in U.S. Pat. No. 7,771,433 to Orbay, which is hereby incorporated by this reference in its entirety for all purposes.

Once bone plate 30 has been properly shaped, pins can be inserted into wire holes 58A and 58B to hold pone plate 30 in position while tibia Ti is prepared to receive fasteners through locking holes 48A-48C, 50 and 52A-52C, as well as through any non-locking compression and multi-directional holes. Kirschner wires (also known as "K-wires") or pins can be used with wire holes 58A and 58B.

Drill guides can be coupled to locking holes 48A-48C, 50 and 52A-52C and holes can be drilled into tibia Ti in order to allow fasteners, such as fasteners 18 of FIG. 1, to be screwed into the drilled bores and threaded into locking bores 48A-48C, 50 and 52A-52C after the drill guides are removed. A fastener need not be coupled to each of locking holes 48A-48C, 50 and 52A-52C. A fastener can be inserted into tibia Ti through compression slot 56 in an orientation desired by the surgeon to best secure bone plate 30 to tibia Ti.

Proximal head 32, in conjunction with strut 36, can provide direct support and reduction to medial condyle 26M to reach bone fragments not directly reachable by bone plates secured to lateral condyle 26L. The pre-shaping of proximal head 32 and distal shaft 34 allows bone plate 30 to cup medial condyle 26M. For example, the offset produced by distance D1 allows proximal head 32 to follow the contour of the anterior portion of medial condyle 26M in order to permit distal shaft 34 to lie against the anterior portion of the diaphysis of tibia Ti. Furthermore, the contouring of proximal head 32 can be customized, such as intraoperatively, by bending of thinned regions 46A-46E. Distal shaft 34 can extend straight down the shaft of tibia Ti to provide anchoring of bone plate 30 to an un-fractured or undamaged portion of tibia Ti.

FIG. 4A is a front view of posterior medial straight bone plate 130, which can include proximal head 132, distal shaft 134 and strut 136. FIG. 4B is a side view of posterior medial straight bone plate 130 of FIG. 4A. FIG. 4C is a top view of posterior medial straight bone plate 130 of FIGS. 4A and 4B.

FIGS. 4A-4C are discussed concurrently. FIGS. 4A-4C show bone plate 130 as being a left-hand specific bone plate. However, bone plate 130 can be configured as a right-hand specific bone plate, such as by producing a bone plate that is a mirror image of bone plate 130.

Proximal head 132 can be shaped to conform to a proximal posterior medial portion of tibia Ti. In particular, proximal head 132 can be configured to conform to the posterior portion of medial condyle 26M of tibia Ti. Proximal head 132 can extend from first head end 138A to second head end 138B. In one example, proximal head 132 can be 2 mm thick.

Distal shaft 134 can extend from first shaft end 140A to second shaft end 140B. Distal shaft 134 can be configured to mate with a posterior medial face of the diaphysis of tibia Ti. In one example, distal shaft 134 can be 3 mm thick.

Proximal head 132 can be elongated along fourth axis A4 and distal shaft 134 can be elongated along fifth axis A5, which can be perpendicular, or near perpendicular, to fourth axis A4. In other examples, proximal head 132 can be disposed at an angle relative to distal shaft 134. In one example, proximal head 132 is approximately 38 mm long along fourth axis A4. It has been found that such a head size can provide sufficient support to the vast majority of tibia sizes. In one example, distal shaft 134 has a length along fifth axis A5 that is in the range of approximately 90 mm to approximately 360 mm in order to accommodate different sized tibias. It has been found that such a shaft size can provide sufficient support to the vast majority of tibia sizes. In one example, distal shaft 134 is 10.75 mm wide relative to fifth axis A5, and proximal head 132 is approximately 9 mm wide at hole portions 144 and approximately 2.5 mm wide at thinned regions 146, relative to fourth axis A4. Strut 136 can connect proximal head 132 with distal shaft 134 to leave open interior region 142.

As seen in FIGS. 4B and 4C, proximal head 132 can be offset from distal shaft 134 via distance D2, as is represented by the offset between sixth axis A6 of proximal head 132 and fifth axis A5 of distal shaft 134. In one example, distance D2 is in the range of approximately 25 mm to approximately 35 mm. Such an offset has been found to be sufficient to wrap around the coronal curvature (i.e., curvature in a coronal plane) of the vast majority of medial condyles.

As seen in FIG. 4C, proximal head 132 also includes an arcuate shape that allows proximal head 132 to wrap around the transverse curvature (i.e., curvature in a transverse plane) of the vast majority of medial condyles. In one example, proximal head 132 sweeps about an arc having a radius that changes relative to fifth axis A5. In one example, the arc can have a radius that is in the range of radius R1A to radius R1B relative to fifth axis A5, wherein R1A to R1B can range from approximately 25 mm to approximately 35 mm along that arc.

Proximal head 132 and strut 136 can each comprise at least one hole portion 144 flanked by at least one of thinned regions 146. In the disclosed embodiment, proximal head 132 can have four hole portions 144A, 144B, 144C and 144D, and strut 136 can have one hole portion 144E. Thinned region 146A can connect hole portion 144A and hole portion 144B. Thinned region 146B can connect hole portion hole portion 144B and hole portion 144C. Thinned region 146C can connect hole portion 144C and hole portion 144D. Thinned region 146C can include scoring 162, which allows hole portion 144D to be more readily removed from hole portion 144C, such as by weakening and subsequent snapping-off of hole portion 144D by a surgeon or another person. Hole portion 144D may alternatively be sawed off or cut off by a surgeon or another person. Thinned region 146D can connect hole portion 144C and hole portion 144E. Thinned region 146E can connect hole portion 144E and distal shaft 134. In particular, thinned region 146E can connect to a mid-section of distal shaft 134. Thinned region 146F can connect hole portion 144A and distal shaft 134. In particular, thinned region 146F can connect to first shaft end 140A.

First head end 138A can connect to first shaft end 140A. First head end 138A can extend generally perpendicularly from distal shaft 134 to the medial side of distal shaft 134. Strut 136 can connect a mid-section of proximal head 132 between first head end 138A and second head end 138B and a mid-section of distal shaft 134 between first shaft end 140A and second shaft end 140B to form interior region 142.

Bone plate 130 can include a plurality of holes to which various fasteners, pins and wires can be connected. Proximal head 132 can include four locking holes 148A, 148B, 148C and 48D. Strut 136 can include locking hole 150. Such a combination of locking holes has been found to be sufficient to reach the majority of the territory of medial condyle 26M with a fixation screw.

Distal shaft 134 can include locking holes 152A, 152B and 152C, multi-directional hole 154, compression slot 156 and wire holes 158A and 158B. Drill guides 160A, 160B, 160C, 160D and 160E are shown connected to locking holes 148A, 148B, 148C and 148D, respectively. Drill guides 160A-160D may comprise drill guides as described in U.S. Pat. No. 8,172,886 to Castaneda et al., which is hereby incorporated by this reference in its entirety for all purposes. In one example, each of locking holes 152A-152C, multi-directional hole 154 and compression slot 156 can be spaced apart by 13 mm. It has been found that such combination of hole types and spacing allows bone plate 130 to be both easily mounted to tibia Ti and to provide sufficient support and reduction to proximal portions of tibia Ti anchored by distal shaft 134.

Locking holes 148A-148D, 150 and 152A-152C can include a threaded bore that allows a threaded shaft of a fastener, such as fasteners 18 of FIG. 1, to pass freely through. The threading of the bore is configured to engage mating threading on the head of the fastener in order to lock the fastener in place with a particular orientation relative to distal shaft 134. In one example, locking holes 148A-148D, 150 and 152A-152C can be configured to receive fixed angle bone fasteners described in U.S. Pat. No. 8,317,842 to Graham et al., which is hereby incorporated by this reference in its entirety for all purposes. In one example, locking holes 148A-148D, 150 and 152A-152C can have a cone shaped and can be configured to accept A.L.P.S. 4.0/3.5 mm screws, which are commercially available from Biomet, Inc. The threading of the bore can also be configured to receive a threading on drill guides 160A-160E.

Multi-directional hole 154 includes a countersink that allows the head of a fastener to recede into hole 154 while being angled relative to distal shaft 134 in a variety of orientations. Thus, multi-directional hole 154 does not lock a fastener into a particular orientation. As such, a surgeon can insert a fastener into hole 154 in a desired orientation to provide support to a specific region of a damaged tibia.

Compression slot 156 comprises an oblong bore, such as an oval or stretched circle, that is configured to receive a fastener and not lock the fastener into a particular orientation in addition to allowing the position of bone plate 130 to be adjusted while being held in place against tibia Ti. Compression slot 156 is also used to provide compression to aid in bone healing.

Wire holes 158A and 158B comprise through-bores that allow pins to be inserted into tibia Ti after the position of bone plate 130 is determined in order to allow other fasteners to be installed through locking holes 148A-148D, 150 and 152A-152C.

Figures 5A, 5B:
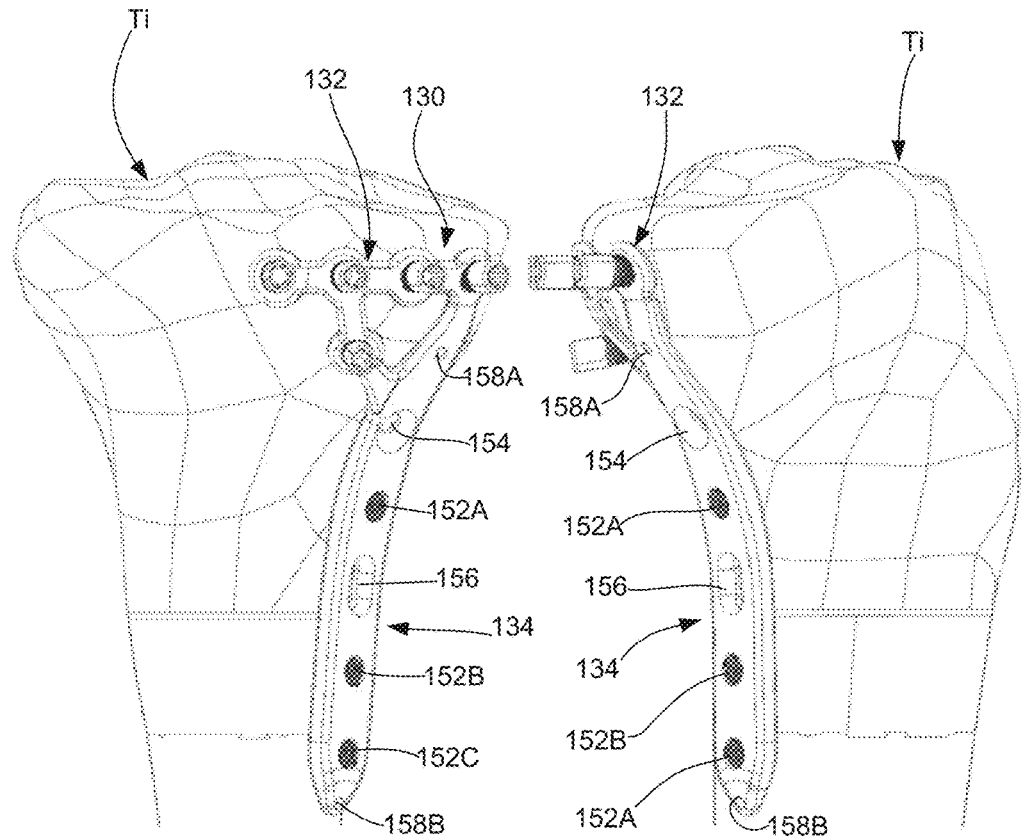
FIG. 5A is a posterior view of a proximal end of a tibia to which the posterior medial straight bone plate of FIGS. 4A-4C is mounted, in accordance with at least one example of the present disclosure.
FIG. 5B is a medial view of the tibia and bone plate of FIG. 5A, in accordance with at least one example of the present disclosure.

FIG. 5A is a posterior view of a proximal end of tibia Ti to which posterior medial straight bone plate 130 of FIGS. 4A-4C is mounted. FIG. 5B is a medial view of tibia Ti and bone plate 130 of FIG. 5A. Proximal head 132 can extend across the posterior side of medial 26M condyle of tibia Ti. Distal shaft 134 can extend across the posterior side of the diaphysis of tibia Ti. As discussed below, thinned regions 146A-146F can be bent to conform to the various surfaces and contours of the medial condyle 26M.

In order to install bone plate 130 on a proximal portion of tibia Ti, a surgeon can first locate the general location on the posterior medial portion of tibia Ti to which bone plate 130 is to be fit. Once in a rough position, in one option, a hole can be drilled in the location of compression slot 156. A fastener can be inserted through compression slot 156 and threaded into the drilled hole. In another option, In another option, wire holes 158A and 158B are first used to secure bone plate 130 to tibia Ti.

Next, hole portions 144A-144E can be adjusted by bending thinned regions 46A-46F. For example, thinned regions 146A-146F can be bent to conform bone plate 130 to the contours of the posterior medial portion of tibia Ti. Drill guides 160A-160D can be used to facilitate bending of bone plate 130, as is described in U.S. Pat. No. 7,771,433 to Orbay, which is hereby incorporated by this reference in its entirety for all purposes.

Once bone plate 130 has been properly shaped, pins can be inserted into wire holes 158A and 158B to hold bone plate 130 in position while tibia Ti is prepared to receive fasteners through locking holes 148A-48D, 150 and 152A-152C, as well as through any multi-directional and non-locking compression holes. Kirschner wires (also known as "K-wires") or pins can be used with wire holes 158A and 158B.

Drill guides can be coupled to locking holes 148A-148D, 150 and 152A-152C and holes are drilled into tibia Ti in order to allow fasteners, such as fasteners 18 of FIG. 1, to be screwed into the drilled bores and threaded into locking bores 148A-148D, 150 and 152A-152C after the drill guides are removed. A fastener need not be coupled to each of locking holes 148A-148DC, 150 and 152A-152C. A fastener can be inserted into tibia Ti through compression slot 156 in an orientation desired by the surgeon to best secure bone plate 130 to tibia Ti.

Proximal head 132, in conjunction with strut 136, can provide direct support and reduction to medial condyle 26M to reach bone fragments not directly reachable by bone plates secured to lateral condyle 26L. The pre-shaping of proximal head 132 and distal shaft 134 allows bone plate 130 to cup medial condyle 26M. For example, the offset produced by distance D2 and the curvature produced by radii R1A and R1B allow proximal head 132 to follow the contour of the posterior portion of medial condyle 26M in order to permit distal shaft 134 to lie against the posterior portion of the diaphysis of tibia Ti. Furthermore, the contouring of proximal head 132 can be customized, such as intraoperatively, by bending of thinned regions 146A-146F. Distal shaft 134 can extend straight down the posterior medial face of the shaft of tibia Ti to provide anchoring of bone plate 130 to an un-fractured or undamaged portion of tibia Ti.

Figures 6A, 6B:
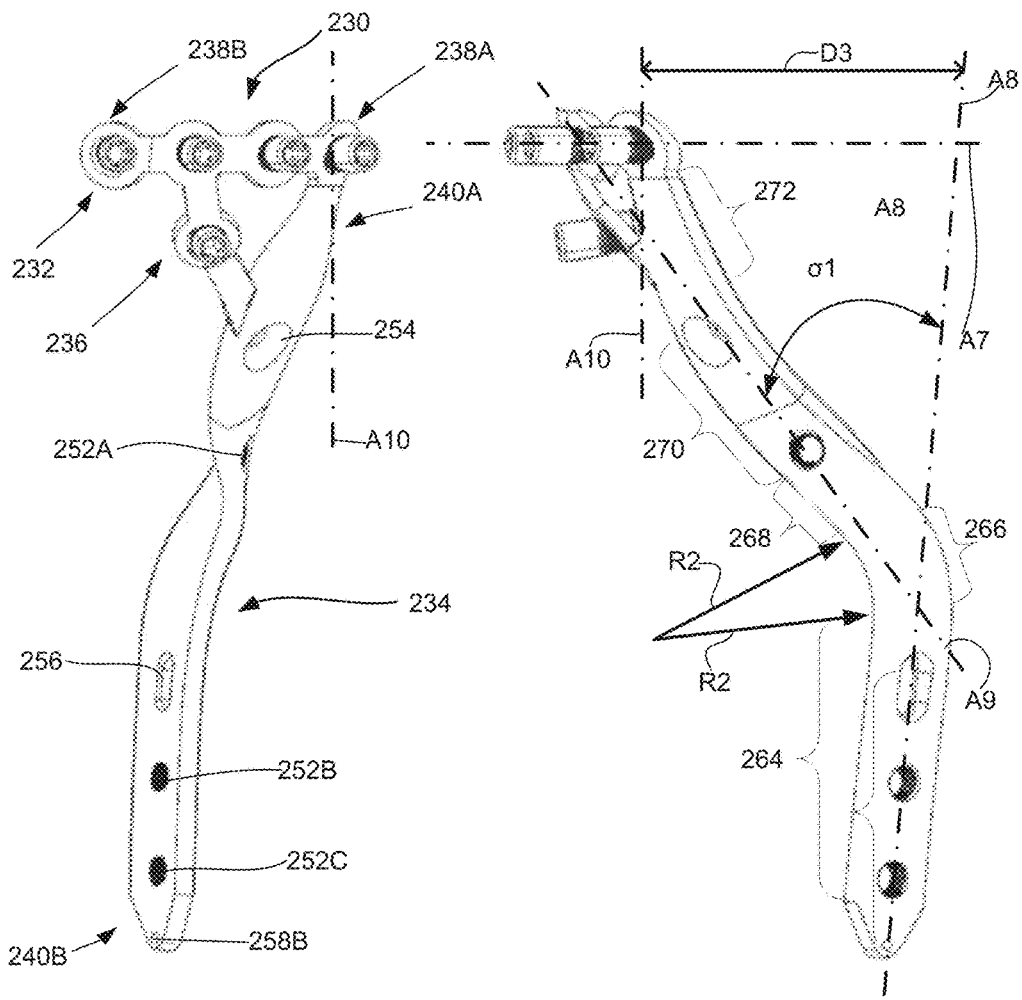
FIG. 6A is a front view of a posterior medial curved bone plate, in accordance with at least one example of the present disclosure.
FIG. 6B is a side view of the posterior medial curved bone plate of FIG. 6A, in accordance with at least one example of the present disclosure.
Figure 6C:
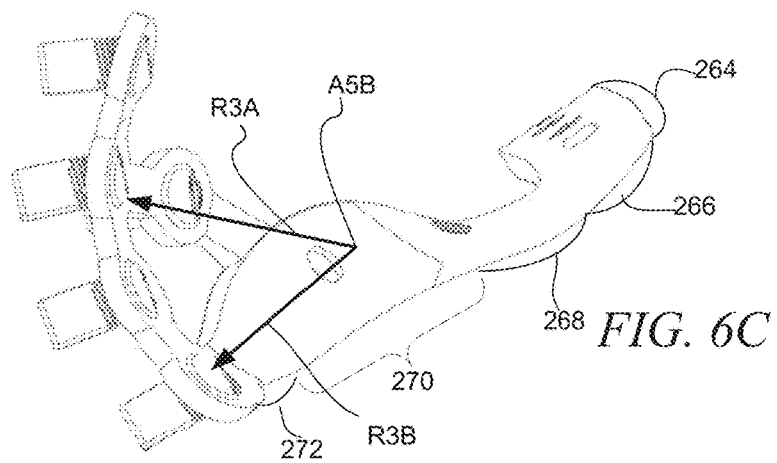
FIG. 6C is a top view of the posterior medial curved bone plate of FIGS. 6A and 6B, in accordance with at least one example of the present disclosure.

FIG. 6A is a front view of posterior medial curved bone plate 230, which can include proximal head 232, distal shaft 234 and strut 236. FIG. 6B is a side view of posterior medial curved plate 230 of FIG. 6A. FIG. 6C is a top view of posterior medial curved plate 230 of FIGS. 6A and 6B. FIGS. 6A-6C are discussed concurrently. FIGS. 6A-6C show bone plate 230 as being a left-hand specific bone plate.

However, bone plate 230 can be configured as a right-hand specific bone plate, such as by producing a bone plate that is a mirror image of bone plate 230.

Proximal head 232 can be shaped to conform to a proximal posterior medial portion of tibia Ti. In particular, proximal head 232 can be configured to conform to the posterior portion of medial condyle 26M of tibia Ti. Proximal head 232 can extend from first head end 238A to second head end 238B. In one example, proximal head 232 can be 2 mm thick.

Distal shaft 234 can extend from first shaft end 240A to second shaft end 240B. In one example, distal shaft 234 can be 3 mm thick. Bone plate 230 is similar to bone plate 130 of FIGS. 4A-5B in features except for the shaping of distal shaft 234. Distal shaft 234 is curved so that it can mate with an anterior medial face of the diaphysis of tibia Ti, rather than a posterior medial face of tibia Ti as is distal shaft 134 of FIG. 5A and 5B. Additionally, the spacing of holes 254, 256 and 252A-252C along distal shaft 234 differs from that of distal shaft 134.

Distal shaft 234 includes distal straight portion 264, curved portion 266, middle straight portion 268, twisted portion 270 and proximal straight portion 272.

Proximal head 232 can extend along seventh axis A7. Distal straight portion 264 of distal shaft 234 can extend along eighth axis A8 and middle straight portion 268 can extend along ninth axis A9. Curved portion 266 can extend from distal straight portion 264 and can have a radius of curvature R2. In one example, radius R2 is in the range of approximately 10 mm to approximately 15 mm. Curved portion 266 can position middle straight portion 268 along ninth axis A9 such that middle straight portion 268 and distal straight portion 264, i.e., ninth axis A9 and seventh axis A7, are disposed at angle σ1 to each other that can be approximately 50 degrees. In one example, distal straight portion 264, curved portion 266 and middle straight portion 268 are all not in the same plane.

Twisted portion 270 can extend from middle straight portion 268 to rotate proximal straight portion 272 about ninth axis A9. In one example, twisted portion 270 can be configured to rotate proximal straight portion 272 relative to the plane in which distal straight portion 264 is disposed.

As seen in FIGS. 6B and 6C, proximal head 232 can be offset from distal shaft 234 via distance D3, as is represented by the offset between tenth axis A10 of proximal head 232 and eighth axis A8 of distal shaft 234. In one example, distance D3 is in the range of approximately 45 mm to approximately 50 mm. Such an offset has been found to be sufficient to wrap around the coronal curvature (i.e., curvature in a coronal plane) of the vast majority of medial condyles.

Proximal straight portion 272 can be positioned to connect with proximal head 232 and strut 236 such that proximal head 232 can be disposed horizontally across medial condyle 26M (FIG. 1).

Proximal head 232 can have a curvature similar to that of proximal head 132 in FIG. 4C. As seen in FIG. 6C, proximal head 232 also includes an arcuate shape that allows proximal head 232 to wrap around the transverse curvature (i.e., curvature in a transverse plane) of the vast majority of medial condyles. In one example, proximal head 232 sweeps about an arc having a radius that changes relative to axis A5B. In one example, the arc can have a radius that is in the range of radius R3A to radius R3B relative to axis A5B, wherein R3A to R3B can range from approximately 25 mm to approximately 35 mm along that arc.

Figure 7A:
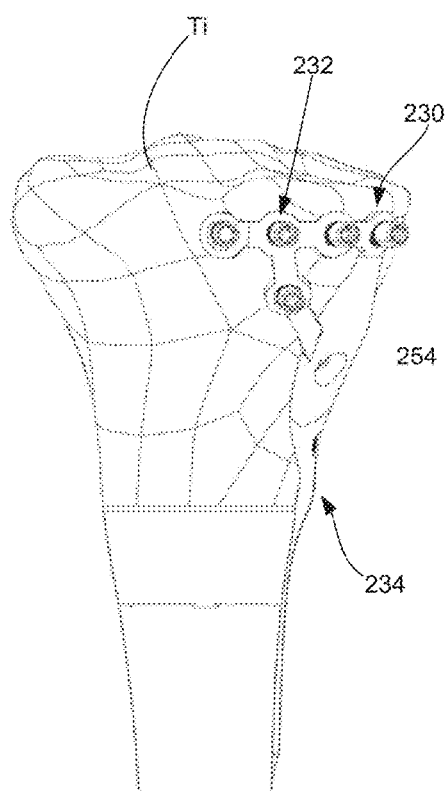
FIG. 7A is a posterior view of a proximal end of a tibia to which the posterior medial curved bone plate of FIGS. 6A-6C is mounted, in accordance with at least one example of the present disclosure.
Figure 7B:
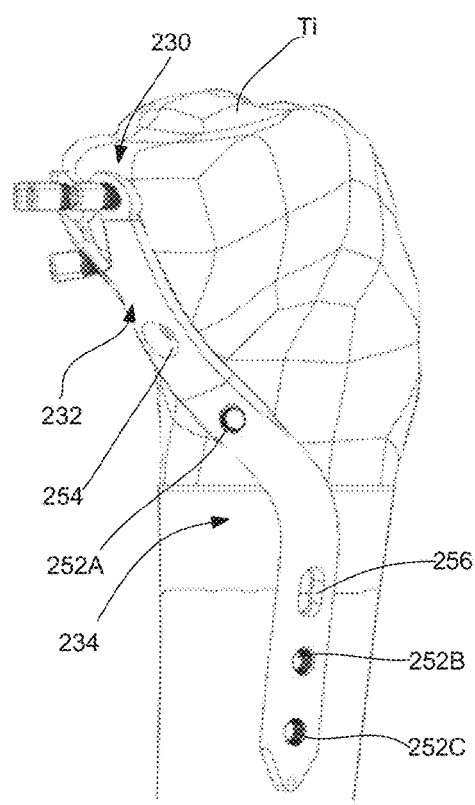
FIG. 7B is a medial view of the tibia and bone plate of FIG. 7A, in accordance with at least one example of the present disclosure.

FIG. 7A is a posterior view of a proximal end of tibia Ti to which posterior medial curved plate 230 of FIGS. 6A-6C is mounted. FIG. 7B is a medial view of tibia Ti and bone plate 230 of FIG. 7A.

Proximal head 232 can extend across the posterior side of medial condyle 26M of tibia Ti. Distal shaft 234 can extend across the posterior side of the diaphysis of tibia Ti. As discussed below, thinned regions 246A-246F can be bent to conform to the various surfaces and contours of the medial condyle 26M. Proximal head 232, in conjunction with strut 236, can provide direct support and reduction to medial condyle 26M to reach bone fragments not directly reachable by bone plates secured to lateral condyle 26L. The pre-shaping of proximal head 232 and distal shaft 234 allows bone plate 230 to cup medial condyle 26M. For example, the offset produced by distance D3 and the curvatures produced by radii R2, R3A and R3B allow proximal head 232 to follow the contour of the posterior portion of medial condyle 26M in order to permit proximal straight portion 272 of distal shaft 234 to lie against the anterior portion of the diaphysis of tibia Ti. Furthermore, the contouring of proximal head 232 can be customized, such as intraoperatively, by bending of thinned regions 246A-246F. Curved portion 266 and twisted portion 270 allow distal straight portion 264 of distal shaft 234 to extend straight down the anterior medial face of the shaft of tibia Ti to provide anchoring of bone plate 230 to an un-fractured or undamaged portion of tibia Ti.

FIG. 8A is a front view of direct medial bone plate 330. FIG. 8B is a top view of direct medial bone plate 330 of FIG. 8A, which can include proximal head 332, distal shaft 334 and struts 336A and 336B. FIGS. 8A and 8B are discussed concurrently. FIGS. 8A and 8B show bone plate 330 as being a left-hand specific bone plate. However, bone plate 330 can be configured as a right-hand specific bone plate, such as by producing a bone plate that is a mirror image of bone plate 330.

Proximal head 332 can include posterior and anterior wings 374A and 374B and can be shaped to conform to a proximal medial portion of tibia Ti. In particular, proximal head 332 can be configured to conform to the direct medial portion of medial condyle 26M of tibia Ti. Proximal head 332 can extend from first head end 338A to second head end 338B. In one example, proximal head 332 can be 2 mm thick.

Distal shaft 334 can extend from first shaft end 340A to second shaft end 340B. Distal shaft 334 can be configured to mate with a medial face of the diaphysis of tibia Ti. Distal shaft 334 can include distal straight portion 376, curved portion 378 and proximal straight portion 380. Distal straight portion 376 can be configured to be placed on an anterior medial face of tibia Ti, while curved portion can be configured to wrap around tibia Ti so that proximal straight portion 380 can be configured to be placed directly on the medial portion of medial condyle 26M.

Curved portion 378 extends from distal straight portion 376 and has a radius of curvature R5. In one example, radius R5 is in the range of approximately 25 mm to approximately 30 mm. Curved portion 378 position and distal straight portion 376 can be disposed at an angle σ2 to each other that can be approximately 140 degrees. In one example, distal straight portion 376, curved portion 378 and proximal straight portion 380 can be in the same plane. In one example, distal shaft 334 can be 3 mm thick.

Proximal head 332 can be elongated along eleventh axis A11 and distal shaft 334 can be elongated along twelfth axis A12 which can be perpendicular to eleventh axis A11. In other examples, proximal head 332 can be disposed at an angle relative to distal shaft 334. In one example, proximal head 332 is approximately 51 mm long along eleventh axis A11. It has been found that such a head size can provide sufficient support to the vast majority of tibia sizes. In one example, distal shaft 334 has a length along twelfth axis A12 that is in the range of approximately 83 mm to approximately 320 mm in order to accommodate different sized tibias. It has been found that such shaft sizes can provide sufficient support to the vast majority of tibia sizes. In one example, distal shaft 334 is 10.75 mm wide relative to twelfth axis A12, and proximal head 332 is approximately 9 mm wide at hole portions 344 and approximately 2.5 mm wide at thinned regions 346, relative to eleventh axis A11. Strut 336 can connect proximal head 332 with distal shaft 334 to leave open interior region 342.

As seen in FIG. 8A, proximal head 332 can be offset from distal shaft 334 via distance D4, as is represented by the offset between thirteenth axis A13 of proximal head 332 and twelfth axis A12 of distal shaft 334. In one example, distance D4 is approximately 28 mm. Such an offset has been found to be sufficient to wrap around the transverse curvature (i.e., curvature in a transverse plane) of the vast majority of medial condyles.

As seen in FIG. 8B, proximal head 332 can be offset from distal shaft 334 via distance D5, as is represented by the offset between eleventh axis A11 of proximal head 332 and twelfth axis A12 of distal shaft 334. In one example, distance D5 is approximately 28 mm. Such an offset has been found to be sufficient to wrap around the coronal curvature (i.e., curvature in a coronal plane) of the vast majority of medial condyles.

As seen in FIG. 8B, proximal head 332 also includes an arcuate shape that allows proximal head 332 to wrap around the transverse curvature (i.e., curvature in a transverse plane) of the vast majority of medial condyles. In one example, proximal head 332 sweeps about an arc having a radius that changes relative to axis A14. In one example, the arc can have a radius that is in the range of radius R4A to radius R4B relative to axis A14, wherein R4A to R4B can range from approximately 25 mm to approximately 45 mm.

Proximal head 332 and strut 336 can each comprise at least one hole portion 344 flanked by at least one of thinned regions 346. In the disclosed embodiment, proximal head 332 can have five hole portions 344A-344E, and struts 336A and 336B can have one hole portion 344F and 344G, respectively.

Thinned region 346A can connect hole portion 344A and hole portion 344B. Thinned region 346B can connect hole portion hole portion 344B and hole portion 344C. Thinned region 346C can connect hole portion 344C and hole portion 344D. Thinned region 346D can connect hole portion 344D and hole portion 344E.

Thinned region 346E can connect hole portion 344B and hole portion 344G. Thinned region 346F can connect hole portion 344G and distal shaft 334. In particular, thinned region 346F can connect to a mid-section of distal shaft 334.

Thinned region 346G can connect hole portion 344D and hole portion 344H. Thinned region 346H can connect hole portion 344H and distal shaft 334. In particular, thinned region 346H can connect to a mid-section of distal shaft 334 opposite thinned region 346G.

Thinned region 346I can connect hole portion 344C with first shaft end 340A of distal shaft 334. Proximal head 332 can extend generally perpendicularly from distal shaft 334 to the medial and lateral sides of distal shaft 334. Struts 336A and 336B can connect mid-sections of wings 374A and 374B to mid-sections of distal shaft 334 between first shaft end 340A and second shaft end 340B to form interior regions 342A and 342B.

Bone plate 330 can include a plurality of holes to which various fasteners, pins and wires can be connected. Proximal head 332 can include five locking holes 348A-348E. Struts 336A and 336B can include locking holes 350A and 350B. Such a combination of locking holes has been found to be sufficient to reach the majority of all of the territory of medial condyle 26M with a fixation screw.

Distal shaft 334 can include locking holes 352A, 352B and 352C, multi-directional hole 354, compression slot 356 and wire holes 358A and 358B. Drill guides 360A-360G are shown connected to locking holes 348A-348E, 350A and 350B, respectively. Drill guides 360A-360G may comprise drill guides as described in U.S. Pat. No. 8,172,886 to Castaneda et al., which is hereby incorporated by this reference in its entirety for all purposes. It has been found that such combination of hole types allows bone plate 330 to be both easily mounted to tibia Ti and to provide sufficient support and reduction to proximal portions of tibia Ti anchored by distal shaft 334.

Locking holes 348A-48E, 350A, 350B and 352A-352C function similarly to locking holes previously discussed herein and separate discussion is omitted for brevity.

Likewise, multi-directional hole 354, compression slot 536 and wire holes 358A and 358B function similarly to the holes and slots previously discussed herein and separate discussion is omitted for brevity.

Figures 9A, 9B:
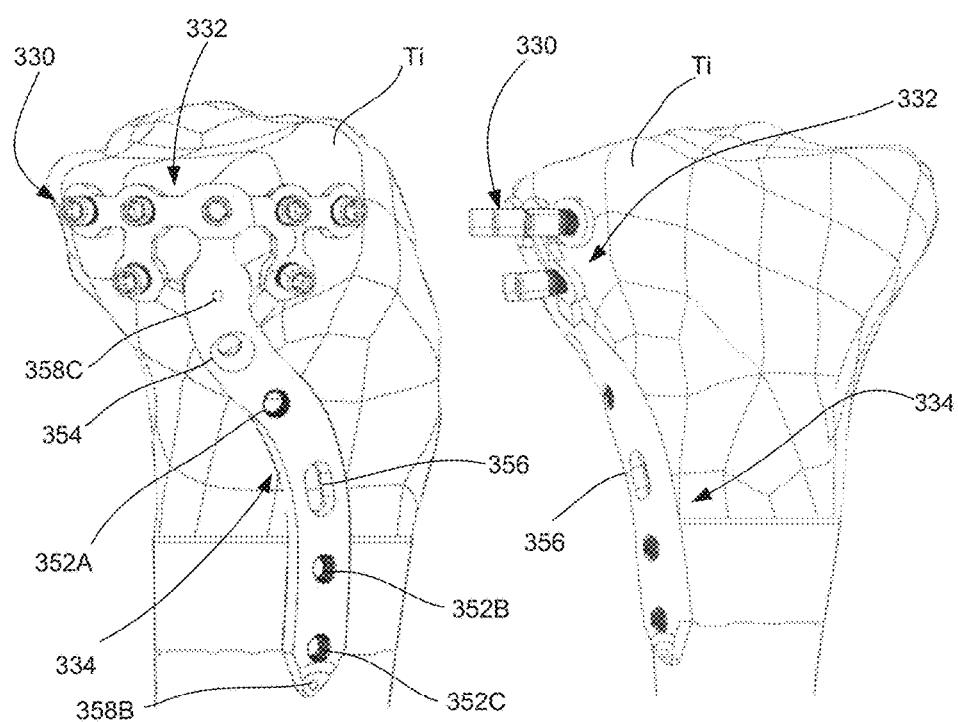
FIG. 9A is a medial view of a proximal end of a tibia to which the direct medial bone plate of FIGS. 8A and 8B is mounted, in accordance with at least one example of the present disclosure.
FIG. 9B is a anterior view of the tibia and bone plate of FIG. 9A, in accordance with at least one example of the present disclosure.

FIG. 9A is a medial view of a proximal end of tibia Ti to which direct medial bone plate 330 of FIGS. 8A and 8B is mounted. FIG. 9B is an anterior view of tibia Ti and bone plate 330 of FIG. 9A.

Proximal head 332 can extend across the direct medial side of medial 26M condyle of tibia Ti. Distal shaft 334 can extend across the anterior medial side of the diaphysis of tibia Ti. As discussed below, thinned regions 346A-346I can be bent to conform to the various surfaces and contours of the medial condyle 26M. Proximal head 332, in conjunction with struts 336A 336B, can provide direct support and reduction to medial condyle 26M to reach bone fragments not directly reachable by bone plates secured to lateral condyle 26L. The pre-shaping of proximal head 332 and distal shaft 334 allows bone plate 330 to cup medial condyle 26M. For example, the offset produced by distances D4 and D5 and the curvature produced by radii R5, R4A and R4B allow proximal head 332 to follow the contour of the medial portion of medial condyle 26M in order to permit proximal straight portion 380 of distal shaft 334 to lie against the direct medial portion of the metaphysis of tibia Ti. Furthermore, the contouring of proximal head 332 can be customized, such as intraoperatively, by bending of thinned regions 346A-346I. Curved portion 378 allow distal straight portion 376 of distal shaft 334 to extend straight down the anterior medial face of the shaft of tibia Ti to provide anchoring of bone plate 330 to an un-fractured or undamaged portion of tibia Ti.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A bone plate comprising:
   a proximal head extending from a first head end to a second head end;
   a distal shaft connected to the proximal head and extending from a first shaft end to a second shaft end; and
   a strut connecting the second end of the proximal head and a mid-section of the distal shaft;
   wherein the first head end is connected to the first shaft end, and the proximal head extends perpendicularly medially from the distal shaft;
   wherein the proximal head is offset from the distal shaft in an anterior direction by approximately 10 millimeters;
   wherein the proximal head is shaped to conform to a proximal medial portion of a tibia;
   wherein the proximal head is shaped to conform to a medial condyle of the tibia; and
   wherein the proximal head is shaped to conform to an anterior medial portion of the medial condyle.

2. The bone plate of claim 1, further wherein the strut connects the proximal head with the distal shaft to leave an open interior region.

3. The bone plate of claim 2, wherein the proximal head and the strut each comprise at least one hole portion flanked by at least one thinned region.

4. The bone plate of claim 3, wherein the proximal head includes at least three locking holes, the strut includes a single locking hole, and the distal shaft portion includes a plurality of locking holes, a multi-directional hole, a compression slot and a wire hole.

5. The bone plate of claim 1, wherein the proximal head includes three locking holes, the strut includes a single locking hole, and the distal shaft portion includes a plurality of locking holes, a multi-directional hole and a compression slot.

6. The bone plate of claim 1 wherein:
   the proximal head has a length in the range of approximately 30 millimeters to approximately 40 millimeters; and
   the distal shaft has a length in the range of approximately 90 millimeters to approximately 360 millimeters;
   the proximal head has a width of approximately 9 millimeters; and
   the distal shaft has a width of approximately 11.5 millimeters.

7. A bone plate comprising:
   a proximal head extending from a first head end to a second head end;
   a distal shaft connected to the proximal head and extending from a first shaft end to a second shaft end;
   a first strut connecting a lateral mid-section of the proximal head portion to a mid-section of the distal shaft; and
   a second strut connecting a medial mid-section of the proximal head portion to the mid-section of the distal shaft;
   wherein a mid-point of the proximal head portion is connected to the first shaft end, and the proximal head extends perpendicularly medially and laterally from the distal shaft;
   wherein the proximal head is shaped to conform to a proximal medial portion of a tibia;
   wherein the proximal head is shaped to conform to a medial condyle of the tibia; and
   wherein the proximal head is shaped to conform to a direct medial portion of the medial condyle.

8. The bone plate of claim 7, wherein the proximal head includes five locking holes, each strut includes a single locking hole, and the distal shaft includes a plurality of locking holes, a multi-directional hole and a compression slot.

9. The bone plate of claim 7, wherein:
   the proximal head is offset from the distal shaft in a medial direction; and
   the mid-section of the distal shaft portion is curved such that the second shaft end of the distal shaft is positionable on an anterior medial side of a tibia.

10. The bone plate of claim 9, wherein:
    the proximal head is offset from the distal shaft in a medial direction by approximately 28 millimeters; and
    the mid-section of the distal shaft portion is curved by a radius of curvature in the range of approximately 25 millimeters to approximately 30 millimeters such that a proximal portion of the distal shaft and a distal portion of the distal shaft are angled relative to each other at an angle of approximately 140 degrees.

11. The bone plate of claim 10, wherein the proximal head is offset from the distal shaft in a posterior direction by approximately 28 millimeters.

12. A bone plate comprising:
a proximal head extending from a first head end to a second head end;
a distal shaft connected to the proximal head and extending from a first shaft end to a second shaft end; and
a strut connecting a mid-section of the proximal head and a mid-section of the distal shaft such that hole portions of the proximal head extends beyond opposite sides of the strut;
wherein the first head end is connected to the first shaft end, and the proximal head extends perpendicularly medially from the distal shaft;
wherein the proximal head is shaped to conform to a proximal medial portion of a tibia;
wherein the proximal head is shaped to conform to a medial condyle of the tibia;
wherein the proximal head is shaped to conform to a posterior medial portion of the medial condyle; and
wherein the proximal head is offset from the distal shaft in a posterior direction in the range of approximately 25 millimeters to approximately 35 millimeters.

13. The bone plate of claim 12, wherein the proximal head includes four locking holes, the strut includes a single locking hole, and the distal shaft includes a plurality of locking holes, a multi-directional hole and a compression slot.

14. The bone plate of claim 12, wherein a proximal-section of the distal shaft is offset from a distal-section of the distal shaft in a posterior direction.

15. The bone plate of claim 14, wherein the mid-section of the distal shaft is curved such that the distal-section and the second shaft end of the distal shaft are positionable on an anterior medial side of a tibia.

16. The bone plate of claim 12, wherein the proximal head has a radius of curvature in the range of approximately 25 millimeters to approximately 35 millimeters relative to an axis of the distal shaft.

17. A bone plate comprising:
a proximal head extending from a first head end to a second head end;
a distal shaft connected to the proximal head and extending from a first shaft end to a second shaft end; and
a strut connecting a mid-section of the proximal head and a mid-section of the distal shaft such that hole portions of the proximal head extends beyond opposite sides of the strut;
wherein the first head end is connected to the first shaft end, and the proximal head extends perpendicularly medially from the distal shaft;
wherein the proximal head is shaped to conform to a proximal medial portion of a tibia;
wherein the proximal head is shaped to conform to a medial condyle of the tibia; and
wherein the proximal head is shaped to conform to a posterior medial portion of the medial condyle;
wherein the proximal head is offset from the distal shaft in a posterior direction;
wherein a proximal-section of the distal shaft is offset from a distal-section of the distal shaft in a posterior direction;
wherein the mid-section of the distal shaft is curved such that the distal-section and the second shaft end of the distal shaft are positionable on an anterior medial side of a tibia; and
wherein the mid-section of the distal shaft is curved by a radius of curvature in the range of approximately 10 millimeters to approximately 15 millimeters such that a proximal portion of the distal shaft and a distal portion of the distal shaft are angled relative to each other at an angle of approximately 50 degrees.

18. The bone plate of claim 17, wherein a proximal-section of the distal shaft is offset from a distal-section of the distal shaft in a posterior direction in the range of approximately 45 millimeters to approximately 50 millimeters.

19. The bone plate of claim 17, wherein the proximal head includes four locking holes, the strut includes a single locking hole, and the distal shaft includes a plurality of locking holes, a multi-directional hole and a compression slot.

20. The bone plate of claim 17, wherein the proximal head has a radius of curvature in the range of approximately 25 millimeters to approximately 35 millimeters relative to an axis of the distal shaft.

* * * * *